US011147539B2

(12) United States Patent
Sornes et al.

(10) Patent No.: US 11,147,539 B2
(45) Date of Patent: Oct. 19, 2021

(54) METHODS AND SYSTEMS FOR BLOOD SPECKLE IMAGING

(71) Applicant: General Electric Company, Schenectady, NY (US)

(72) Inventors: Anders Rasmus Sornes, Oslo (NO); Stian Langeland, Horten (NO)

(73) Assignee: General Electric Company, Schenectady, NY (US)

( * ) Notice: Subject to any disclaimer, the term of this patent is extended or adjusted under 35 U.S.C. 154(b) by 789 days.

(21) Appl. No.: 15/707,172

(22) Filed: Sep. 18, 2017

(65) Prior Publication Data
US 2019/0083068 A1 Mar. 21, 2019

(51) Int. Cl.
*A61B 8/08* (2006.01)
*A61B 8/06* (2006.01)
*A61B 8/14* (2006.01)
*A61B 8/00* (2006.01)

(52) U.S. Cl.
CPC .............. *A61B 8/5223* (2013.01); *A61B 8/06* (2013.01); *A61B 8/5207* (2013.01); *A61B 8/5253* (2013.01); *A61B 8/145* (2013.01); *A61B 8/463* (2013.01); *A61B 8/469* (2013.01); *A61B 8/488* (2013.01)

(58) Field of Classification Search
CPC ........... A61B 8/00; A61B 8/06; A61B 8/5207; A61B 8/5223; A61B 8/5253; A61B 8/145; A61B 8/463; A61B 8/469; A61B 8/488
See application file for complete search history.

(56) References Cited

U.S. PATENT DOCUMENTS 6,014,473 A * 1/2000 Hossack ................ A61B 8/145
348/169
6,224,552 B1 * 5/2001 Jago ........................ A61B 8/00
600/437

(Continued)

OTHER PUBLICATIONS

Jiang, Wei, Jeffrey P. Astheimer, and Robert C. Waag. "Aberration compensation of an ultrasound imaging instrument with a reduced numbers of channels." IEEE transactions on ultrasonics, ferroelectrics, and frequency control 59, No. 10 (2012): 2210-2225.*

(Continued)

Primary Examiner — Carolyn A Pehlke
(74) Attorney, Agent, or Firm — The Small Patent Law Group LLC; Philip S. Hof

(57) ABSTRACT

The systems and methods generally relate to blood speckle imaging. The systems and methods transmit a plurality of transmit (Tx) beams from an ultrasound probe to a region of interest (ROI). The plurality of Tx beams are transmitted successively with respect to each other. At least two of the plurality of Tx beams overlap at a common position. The systems and methods estimate velocity fields from the speckle tracking, and weight the velocity fields based on weighting signals to form weighted velocity fields. The weighting signal being centered at transmit beam axes of the plurality of Tx beams. The systems and methods interpolate the weighted velocity fields that overlap at the common position to adjust a portion of the weighted velocity fields, and generate an image on a display of a combined velocity field by combining the weighted velocity fields.

20 Claims, 10 Drawing Sheets

(56) References Cited

U.S. PATENT DOCUMENTS

| | | | |
|---|---|---|---|
| 6,554,770 B1* | 4/2003 | Sumanaweera | A61B 8/0833 |
| | | | 600/443 |
| 6,666,823 B2 | 12/2003 | Yao | |
| 8,475,380 B2 | 7/2013 | Kristoffersen et al. | |
| 2003/0158483 A1* | 8/2003 | Jackson | A61B 8/0883 |
| | | | 600/449 |
| 2015/0289837 A1* | 10/2015 | Kim | A61B 8/5223 |
| | | | 600/454 |
| 2018/0028154 A1* | 2/2018 | Zhai | A61B 5/207 |
| 2018/0253854 A1* | 9/2018 | Falahatpisheh | A61B 8/466 |

OTHER PUBLICATIONS

Fadnes, Solveig, Ingvild Kinn Ekroll, Siri Ann Nyrnes, Hans Torp, and Lasse Lovstakken. "Robust angle-independent blood velocity estimation based on dual-angle plane wave imaging." IEEE transactions on ultrasonics, ferroelectrics, and frequency control 62, No. 10 (2015): 1757-1767.*

O'Donnell, Matthew, Andrei R. Skovoroda, Benjamin M. Shapo, and Stanislav Y. Emelianov. "Internal displacement and strain imaging using ultrasonic speckle tracking." IEEE transactions on ultrasonics, ferroelectrics, and frequency control 41, No. 3 (1994): 314-325.*

Bohs, L. N., B. J. Geiman, M. E. Anderson, S. C. Gebhart, and G. E. Trahey. "Speckle tracking for multi-dimensional flow estimation ." Ultrasonics 38, No. 1-8 (2000): 369-375.*

* cited by examiner

METHODS AND SYSTEMS FOR BLOOD SPECKLE IMAGING

FIELD

Embodiments described herein generally relate to blood speckle imaging.

BACKGROUND OF THE INVENTION

During an ultrasound exam, a velocity field is estimated by performing speckle tracking between repeated acquisitions performed by a conventional ultrasound imaging system. The speckle tracking detects motion between successive clutter filtered B-mode frames of ultrasound data. The B-mode frames need to be acquired repeatedly in succession in order to detect the speckle pattern displacement over time. Moreover a region of interest (ROI) may typically have to be subdivided into several adjacent subsections where such a displacement detection by repeated firing is performed in succession from one side of the ROI to the other. This method for detecting the velocity field for the entire ROI has the inherent problem that since the recording and detection must occur with a delay between different subsections of the ROI, the velocity field estimated in the ultrasound exam will be laterally composed of subsections recorded at slightly different instances, between which there are time gaps. The time gaps represent borders of two such subsections, corresponding to different transmit beam directions of an ultrasound probe. Each subsection will be composed of data from a number of parallel receive beams or MLAs that represents simultaneously acquired data from one transmit direction, repeated a predefined number of times, that covers the area of the subsection. The speckle pattern set up by the moving particles will be uncorrelated between two subsections due to this time difference. Hence for particles close to the borders of a subsection it is not known from where they came or to where they are going. Even though the velocity of the particles is more slowly varying than the patterns and hence is more correlated from subsection to subsection, estimates of the velocity field at the time gaps represent discontinuities of the motion for the speckle tracking. Moreover the lack of good estimate at the border is forming a gray zone. The gray zone represents a portion of the ultrasound image where the velocity field is not known.

For example, the motion in the region of interest can be detected only at certain positions during a finite time interval. A velocity at positions along an edge of the subsection covered by one transmit direction or scan of the ultrasound imaging system cannot be estimated. The positions along the edge represent points whose lateral movements are not known and form the gray zone.

BRIEF DESCRIPTION OF THE INVENTION

In an embodiment a method (e.g, for speckle tracking) is provided. The method includes transmitting a plurality of transmit (Tx) beams from an ultrasound probe to a region of interest (ROI). The plurality of Tx beams are transmitted successively with respect to each other. The plurality of Tx beams are configured to acquire ultrasound data for speckle tracking by repeatedly firing along the Tx beams. At least two of the plurality of Tx beams overlap at a common position. The method includes estimating velocity fields from the speckle tracking and weighting the velocity fields based on weighting signals to form weighted velocity fields. The weighting signal being centered at transmit beam axes of the plurality of Tx beams. The method includes interpolating the weighted velocity fields that overlap at the common position to adjust a portion of the weighted velocity fields The method includes generating an image of a combined velocity field on a display by combining the weighted velocity fields.

In an embodiment a system (e.g., a medical imaging system) is provided. The system includes an ultrasound probe configured to acquire ultrasound data for speckle tracking, a display, and a controller circuit. The controller circuit is configured to instruct the ultrasound probe to transmit a plurality of transmit (Tx) beams to a region of interest (ROI). The plurality of Tx beams are transmitted successively with respect to each other. The plurality of Tx beams are configured to acquire ultrasound data for speckle tracking by repeatedly firing along the Tx beams. At least two of the plurality of Tx beams overlap at a common position. The controller circuit is configured to estimate velocity fields from the speckle tracking and weight the velocity fields based on weighting signals to form weighted velocity fields. The weighting signal being centered at transmit beam axes of the plurality of Tx beams. The controller circuit is configured to interpolate the weighted velocity fields that overlap at the common position to adjust a portion of the weighted velocity fields The controller circuit is configured to generate an image of a combined velocity field on the display by combining the weighted velocity fields.

In an embodiment a method (e.g, for speckle tracking) is provided. The method includes transmitting a plurality of transmit (Tx) beams from an ultrasound probe to a region of interest (ROI). The plurality of Tx beams are transmitted successively with respect to each other. The plurality of Tx beams are configured to acquire ultrasound data for speckle tracking by repeatedly firing the plurality of Tx beams. At least two of the plurality of Tx beams overlap at a common position. The method includes weighting the velocity fields estimated from ultrasound data based on weighting signals to form weighted velocity fields estimated from ultrasound data. The weighting signal being centered at transmit beam axes of the plurality of Tx beams. The method includes identifying non-collinear ultrasound data from the ultrasound data, and generating at least one sub-image from the non-collinear ultrasound data. The method also includes weighting and interpolating velocity fields estimated from ultrasound data recorded along receive lines that are non-collinear between the sub-images as long as the spatial region the lines cover overlap. The velocity values at corresponding points in the sub-images within the overlap region may be estimated from knowledge of the velocity field and subsequently be interpolated between the sub-images. The method includes interpolating the weighted velocity fields derived from ultrasound data that overlap at the common position. The velocity field includes at least two sectors and represent a two dimensional blood velocity of the ROI. At least one of the velocity fields is estimated based on interpolating the ultrasound data of the at least one sub-image with a portion of the weighted ultrasound data. The method includes generating a smooth velocity field visualization on a display by combining the velocity fields.

DETAILED DESCRIPTION OF THE INVENTION

Figure 1:
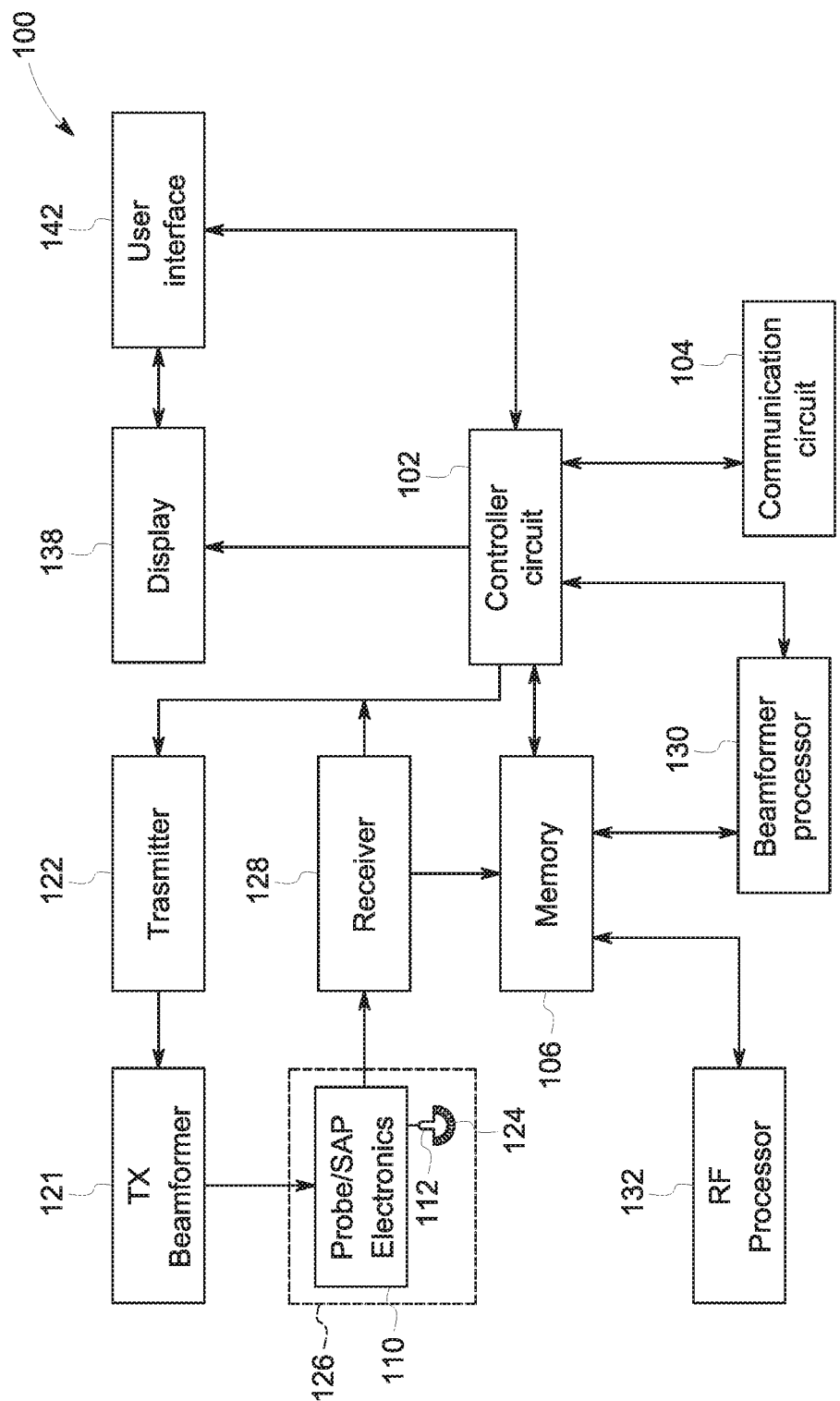
FIG. 1 illustrates a schematic block diagram of an embodiment of a medical imaging system.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments described herein generally relate to speckle imaging. A medical imaging system directs a plurality of successive transmissions from an ultrasound probe. The successive transmissions are utilized in connection with multiple line acquisitions (MLA) and/or parallel receive lines. The MLA is utilized to acquire ultrasound data to form a sub section of the entire image with a certain lateral extension covering the transmit beam. Repeated acquisitions of the same transmit direction in the course of this succession may be used to speckle track the ultrasound pattern over time and estimate a velocity field. The velocity field represents a two dimensional (2D) measurement of blood velocity and/or motion across a region of interest (ROI). The successive transmissions in the different directions partially overlap at one or more common positions within the ROI. For example, the medical imaging system configures the MLA beam layout such that receive lines for at least one transmit beam overlap with a spatially coincidental receive line from one or more successive transmit beams. Additionally, the layout of the MLAs are defined such that velocity data is collected for at least one transmit event at any given point avoiding gray zones. The ultrasound data of a group of MLAs in the scan plane of the ultrasound probe allows overlap with data from the interior of another beam of the MLA. This allows the estimation of the velocity field at the same spatial location for two or more individual MLA groups recorded at different times. Interpolation may be performed between these estimates of the velocity at a particular location to prevent discontinuities in the velocity field from appearing at transitions between the MLA groups and allows a spatially smooth and continuous field to be displayed.

The partial overlapping of the successive transmissions of the MLA group allows an interpolation of the velocity field at the one or more common positions. For example, the medical imaging system is configured to interpolate in time the velocity field between successive time instances across a time scale of the scan acquisition so that a continuous smooth output field of the speckle image can be displayed.

Additionally or alternatively, the medical imaging system is configured to shift the receive lines. For example, the receive lines of different MLAs position along common positions can be affected by differences in arrival times for the transmitted wavefront at the particular orientation of the MLA with respect to the transmit beam axis. The medical imaging system is configured to radially shift the receive lines representing the common location to compensate differences in transmit wavefront arrival time such that the received lines are aligned with each other.

A technical effect of at least one embodiment described herein enables a smooth velocity field to be generated. A technical effect of at least one embodiment described herein provides a speckle tracking image with less artifacts and errors visible to the user.

Terms

The term "ultrasound exam" refers to an acquisition of one or more ultrasound images of one or more anatomical structures. The ultrasound exam can represent a continuous and/or discontinuous acquisition of one or more ultrasound images (e.g., 2D, 3D, 4D) during a scan of a patient. The scan of the patient may last up to a minute and/or an hour. Optionally, the ultrasound exam can be based on one or more protocols.

The term "collinear ultrasound data" is used to refer to ultrasound data collected along at least two receive lines that are associated with successive ultrasound transmit signals and that correspond to a common physical position.

The term "non-collinear ultrasound data" is used to refer to ultrasound data collected along at least two receive lines associated with successive ultrasound transmit signals and that correspond to different positions.

The term "real time" or "real-time" is used to refer to an operation, action, and/or process performed by the medical imaging system (e.g., a controller circuit) during an ultrasound exam. An ultrasound exam may include collection of multiple separate 2D or 3D ultrasound images for a common or different view windows. Optionally, the ultrasound exam may include collection of one or more cine loops of 2D or 3D ultrasound data. The operation, action or process may be performed while actively scanning a patient and/or between separate scanning operations that occur during a single ultrasound exam. A length of time associated with real time, and may vary based on a processing speed and/or operating specification (e.g., no intentional lag or delay). Real time includes updating an ultrasound image shown on the display after each ultrasound pulse within a scan and/or after each ultrasound scan sequence. Additionally or alternatively, ultrasound data may be stored temporarily in memory of the medical imaging system during the ultrasound exam and processed in a live or off-line operation.

FIG. 1 illustrates a schematic block diagram of an embodiment of a medical imaging system 100. For example, the medical imaging system 100 is shown as an ultrasound imaging system. The medical imaging system 100 may include a controller circuit 102 operably coupled to a communication circuit 104, a display 138, a user interface 142, an ultrasound probe 126, and a memory 106.

The controller circuit 102 is configured to control the operation of the medical imaging system 100. The controller circuit 102 may include one or more processors. Optionally, the controller circuit 102 may include a central processing unit (CPU), one or more microprocessors, a graphics processing unit (GPU), or any other electronic component capable of processing inputted data according to specific logical instructions. Optionally, the controller circuit 102 may include and/or represent one or more hardware circuits or circuitry that include, are connected with, or that both include and are connected with one or more processors, controllers, and/or other hardware logic-based devices. Additionally or alternatively, the controller circuit 102 may execute instructions stored on a tangible and non-transitory computer readable medium (e.g., the memory 106).

The controller circuit 102 is configured to instruct the ultrasound probe 126 to emit successive Tx beams from a transducer array 112 during an ultrasound exam. Echoes from the regions insonified by the Tx beams may be acquired by MLAs or parallel receive lines recorded by a transducer array 112 of the ultrasound probe 126. The Tx beams are configured to acquire ultrasound data of a region of interest (ROI) 201. The ROI 201 may represent a portion of a heart, typically covering the chambers of the heart and the myocardia or it may cover other vessels containing blood in motion.

The ultrasound data may represent repeated B-mode type of ultrasound imaging data but typically clutter filtered temporally in order to enhance moving particles even if they are weak, such as blood. For example, the controller circuit 102 generates sub-images based on the ultrasound data. The sub-images represent the ultrasound data that includes a speckle pattern. The controller circuit 102 may apply a clutter filtering to the speckle pattern. The clutter filtering can occur during the beamforming and/or subsequent to the beamforming. The clutter filtering extracts a blood component from the sub-image and calculates a time delay between transmit and receive beamforming time delays. The controller circuit 102 applies the time delay correction to the speckle patter within the sub-image to enhance motion of the speckle tracking. The clutter filtering may be performed on the sub-image prior to identifying the speckle tracking. The speckle pattern is used to track the motion of the blood within the chambers of the heart or other vessels of interest, but it may also be used to track moving tissue for instance myocardial motion of the heart. The motion of the speckles over time are tracked by the controller circuit 102 to form a velocity field. For example, the motion of the speckles represents a velocity field indicative of a 2D dimensional blood velocity.

Figure 2A:
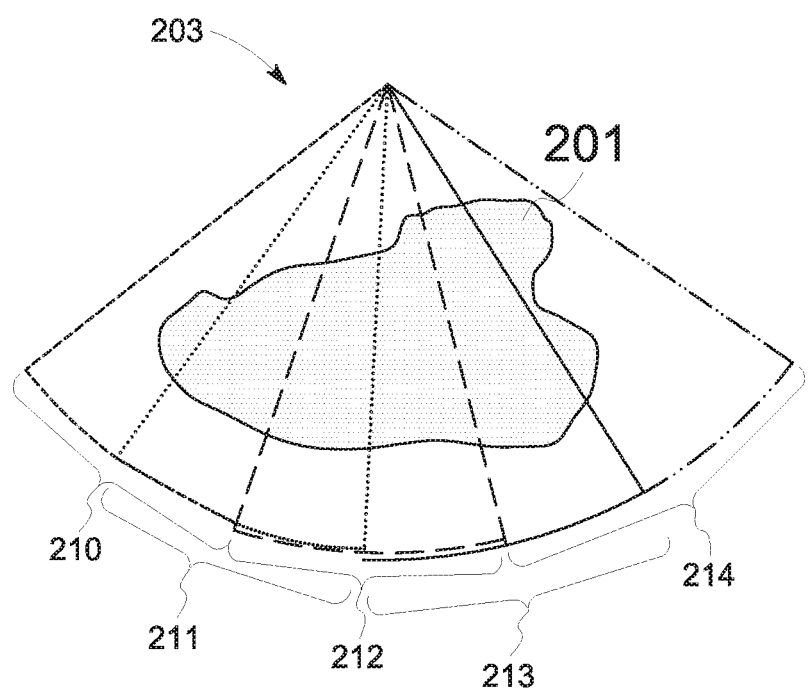
FIG. 2A illustrates an embodiment of a scan region.

FIG. 2A illustrates an embodiment of a scan region 203. The scan region 203 includes the ROI 201. The scan region 203 is subdivided into sectors 210-214. Each of the sectors 210-214 overlap with at least one adjacent sector 210-214. For example, the sector 210 overlaps with the sector 211, the sector 211 overlaps with sectors 210, 212, the sector 212 overlaps with sectors 211, 213, the sector 213 overlaps with the sectors 212, 214, and the sector 214 overlaps with the sector 213. The controller circuit 102 instructs the ultrasound probe 126 to fire and/or transmit n (e.g., more than one) a plurality of transmit (Tx) beams within each sector 210-214 representing different MLA groups. For example, the controller circuit 102 instructs the ultrasound probe 126 to fire and/or transmit at least two Tx beams within each sector 210-214. Additionally or alternatively, the amount of overlap shown in FIG. 2A may be different between the sectors 210-214. The receive lines in response to the Tx beam will overlap with each other as shown in FIG. 2B.

Figure 2B:
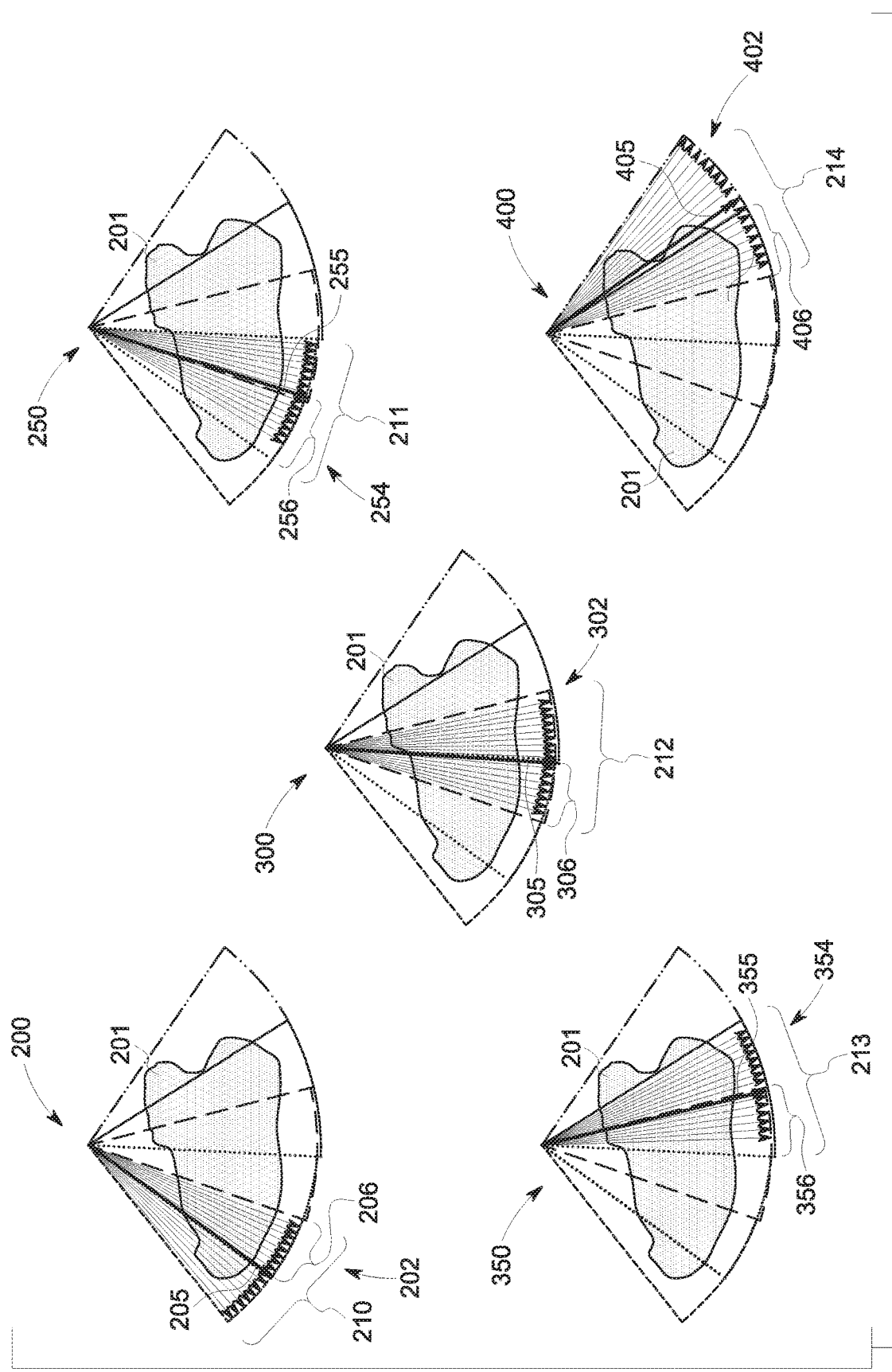
FIG. 2B illustrates an embodiment of acquisition frames of a region of interest.

FIG. 2B illustrate embodiments of acquisition frames 200, 250, 300, 350, 400 of the ROI 201. Each sector 210-214 includes a corresponding at least two successive Tx beams 205, 255, 305, 355, 405. It may be noted that although one Tx beam is shown in FIG. 2A, at least two successive Tx beams (e.g., n successive firings by the ultrasound probe 126) are fired and/or transmitted by the ultrasound probe 126 for each of the sectors 210-214. The Tx beams 205, 255, 305, 355, 405 are configured to acquire ultrasound data for speckle tracking. For example, the ultrasound probe 126 repeatedly fires (e.g., more than two) the plurality of Tx beams (e.g., the at least two successive Tx beams 205, 255, 305, 355, 405) within each of the sectors 210-214. Optionally, the Tx beams 205, 255, 305, 355, 405 may represent more than two successive Tx beams fired by the ultrasound probe 126 within each of the sectors 210-214. The Tx beams 205, 255, 305, 355, 405 are shown laterally in FIG. 2B. The Tx beams 205, 255, 305, 355, 405 may also be transmitted radially from the ultrasound probe 126. The acquisition frames 200, 250, 300, 350, 400 are subdivided into the sectors 210-214. The plurality of Tx beams 205, 255, 305, 355, 405 are successively transmitted from the ultrasound probe 126 at each of the sectors 210-214. For example, the controller circuit 102 instructs the ultrasound probe 126 to fire at least two successive Tx beams 205 in the sector 210 and receives ultrasound data along the receive lines 202, immediately afterwards, the ultrasound probe 126 fires at least two successive Tx beams 255 in the sector 211 and receives ultrasound data along the receive lines 254, immediately afterwards, the ultrasound probe 126 fires at least two successive Tx beams 305 in the sector 211 and receives ultrasound data along the receive lines 302. The process is repeated for all of the sectors 210-214, such that ultrasound data is acquired from all of the sectors 210-214. The movement of the speckle pattern recorded at any place within the MLA groups (e.g., acquisition frames 200, 250, 300, 350, 400), can be detected from the ultrasound data for speckle tracking.

The acquisition frames 200, 250, 300, 350, 400 include the receive lines 202, 254, 302, 354, 402, respectively, generated in response to the corresponding at least two successive Tx beams 205, 255, 305, 355, 405. It may be noted that the receive lines 202, 254, 302, 354, 402 overlap with at least one alternative receive line 202, 254, 302, 354, 402 at the one or more common positions. Optionally, the receive lines 202, 254, 302, 354, 402 may represent multiple acquisitions within the sectors 210-214 from the at least two successive Tx beams 205, 255, 305, 355, 405. As noted the sectors 210-214 overlap with at least one adjacent sector 210-214 such that at least a portion of the MLA lines (e.g., the receive lines 202, 254, 302, 354, 402) overlap at one or more common positions. For example, the receive lines 202 of the sector 210 overlap at common positions with the receive lines 255 of the sector 211. The one or more common positions are shown as the overlap portions 206, 256, 306, 356, 406 of the sectors 210-214.

Based on the ultrasound data received along the receive lines 202, 254, 302, 354, 402, the controller circuit 102 estimates the velocity field in each region. For example, the controller circuit 102 analyzes the ultrasound data acquired along the receive lines 202, 254, 302, 354, 402 to identify motion (e.g., speckle tracking) in the ROI 201 locally in the area acquired by repeated fire of each of the Tx beams 205, 255, 305, 355, 405. For example, the controller circuit 102 receives ultrasound data for each of the sectors 210-214 from the receive lines 202, 254, 302, 354, 402. The motion is calculated by the controller circuit 102 for the speckle tracking is acquired from the repeated firing of the at least two successive Tx beams 205, 255, 305, 355, 405 along each direction and/or the sector 210-214, individually. For example, the controller circuit 102 determines the speckle tracking from the ultrasound data acquired along the receive lines 202 from the at least two successive Tx beams 205 for the sector 210. Subsequently, the controller circuit 102 determines the speckle tracking form the ultrasound data acquired along the receive lines 254 from the at least two successive Tx beams 255 for the sector 211. The speckle tracking for the sectors 210-214 is identified by the controller circuit 102 and represents the 2D dimensional blood velocity. Additionally, the controller circuit 102 interpolates in time the velocity fields from overlapped receive lines 202, 254, 302, 354, 402.

The at least two successive Tx beams 205, 255-305, 355, 405 are shown being transmitted along different directions relative to the ultrasound probe 126 correspdoning to the different sectors 210-214 and/or different beam axes. The controller circuit 102 interpolates the velocity field estimated from the ultrasound data for the overlapping portions 206, 256, 306, 356, 406 of the receive lines 202, 254, 302, 354, 402 based on a weighting signal.

Optionally, the controller circuit 102 may register the receive lines 202, 254, 302, 354, 402 to correct for shifts in radial registration of events due to transmit wavefront arrival time differences relative to each other. For example, the receive lines 202 may be shifted based on geometrical differences caused by the transmit to receive beam distance. A focused Tx beam will produce a curved wavefront that will hit different receive lines at different times depending on how far the receive line is from the transmit beam axis (e.g., a location of the at least two successive Tx beams 205, 255, 305, 355, 405 within the sectors 210-214). The controller circuit 102 compensates the ultrasound data radially along the receive lines 202, 254, 302, 354, 402, for the small delays produced by the geometrical differences. The controller circuit 102 identifies one or more wavefronts in space at each receive point along the receive lines 202, 254, 302, 354, 402. The wavefront is indicative of when in time ultrasound data along the receive lines 202, 254, 302, 354, 402 are received by the ultrasound probe 126. The controller circuit 102 adjusts the one or more wavefronts of the receive lines 202, 254, 302, 354, 402 radially based on a registration model 502.

A distance between the receive lines 202, 254, 302, 354, 402 and the at least two successive Tx beams 205, 255, 305, 355, 405 may give rise to a slight misregistration of the location of the echoes (e.g., blood particles) in different parts of the sectors 210-215. The misregistration is based on where the transmit beam axes is located, and is due to the different arrival times of the curved transmitted wavefront at the particular receive points at the ROI 201. The registration model 502 is configured to correct for the misregistration. The controller circuit 102 corrects the ultrasound data radially based on the registration model to improve the accuracy of the velocity estimates for the speckle tracking. It may be noted that the correction by the controller circuit 102 may occur after and/or during receive beamforming (e.g., prior to speckle tracking data acquisition). The correction by the controller circuit 102 ensures that the interpolation of multiple estimates of the velocity field described herein is optimally aligned and have as little discrepancy as possible.

Figure 3:
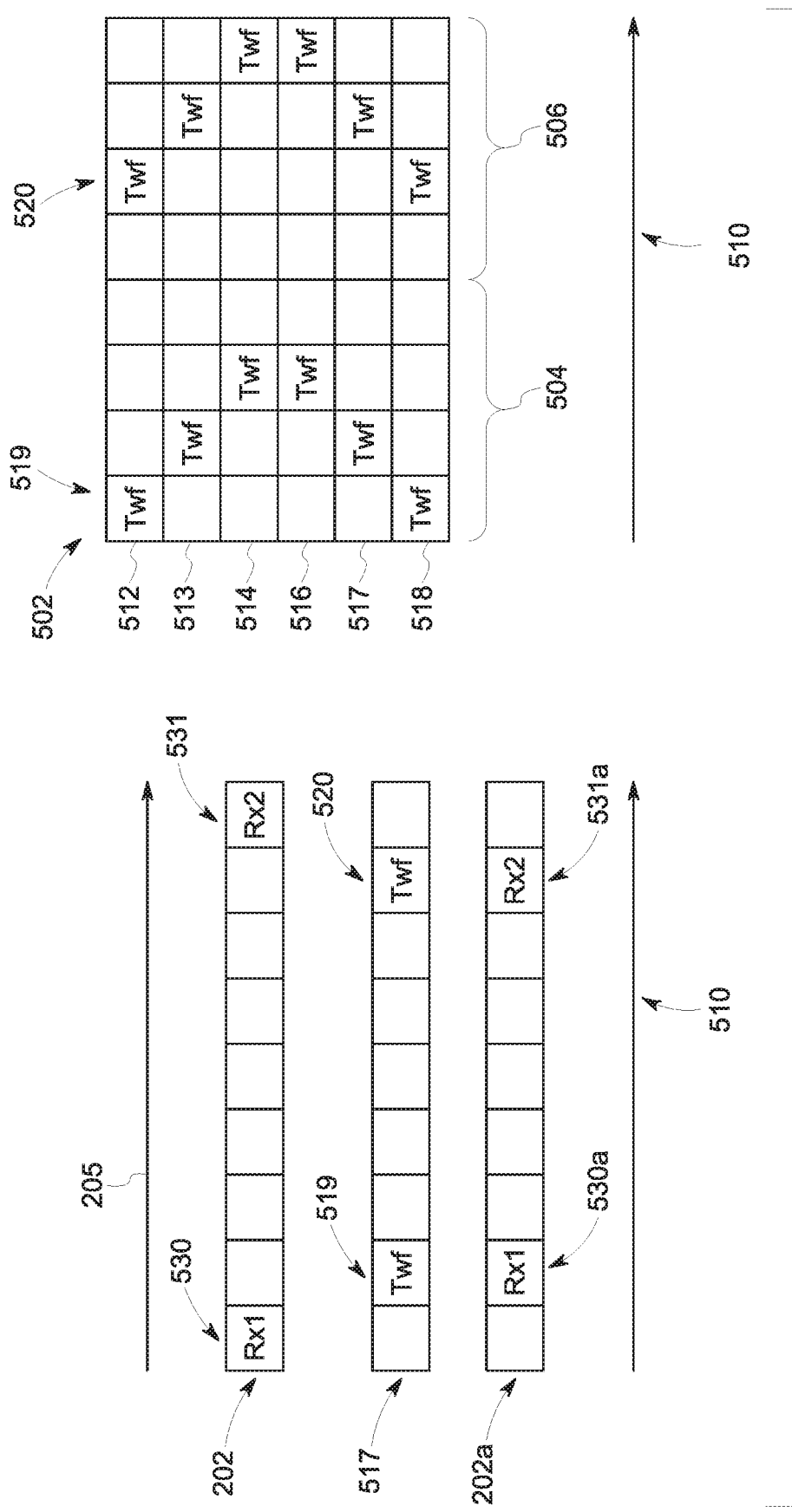
FIG. 3 illustrates an embodiment of a registration model and ultrasound data of a receive line.

FIG. 3 illustrates an embodiment of the registration model 502 and the ultrasound data of one of the receive lines 202a. The registration model 502 is based on priori information stored in the memory 106. For example, the priori information may represent the registration model 502 of the ROI 201 at a corresponding depth and/or position of the ROI 201 relative to the ultrasound probe 126. The depth scan may be based on the acquisition settings of the ultrasound probe 126 and/or a position of the ROI 201 within a patient. The registration model 502 includes estimations on when ultrasound data along the receive lines 202, 254, 302, 354, 402 will be received by the ultrasound probe 126 relative to corresponding Tx beams 205, 252, 305, 355, 405. The ultrasound data of the receive lines 202, 254, 302, 354, 402 at the common position are aligned by the controller circuit 102 based on the registration model 502. The registration model 502 is configured to check for temporal sifts of the receive lines 202, 254, 302, 354, 402, such that the receive lines 202, 254, 302, 354, 402 are corrected for each receive line due to the curvature of the ultrasound probe 126 and/or the depth of the ROI 201. The correction of the receive lines 202, 254, 302, 354, 402 compensates for the radial difference between the arrival time of the wavefront at the receive line locations and at the transmit beam axes. The transmit beam axes correspond to a position of the at least two successive Tx beams 205, 252, 305, 355, 405 within the sectors 210-214.

The registration model 502 includes receive lines 512-518. The receive lines 512-518 are shown over time 510 with estimation on when baseline target points insonified by the transmit wavefronts 519-521 are received by the ultrasound probe 126. The estimations of when the baseline targets are insonified by the wavefronts 519-521 are based on the depth of the sample position in the ROI 201, the distance between receive line and transmit beam axes, and the characteristics (e.g., focus, aperture, apodization) of the transmit beam. For example, the registration model 502 is shown in action at two of the points along the receive line at 504 and 506. The sample locations 504 and 506 corresponds to places in the ROI 201 that have different characteristics that affect the registration of objects of the receive lines 512-518 in different manners. The registration model 502 estimates when the baseline targets insonified by the transmit wavefronts 519-521 of the receive lines 512-518 are received by the ultrasound probe 126. For example, the time estimates (Twf) may represent peaks of the transmit wavefronts 519-521 along the receive lines 512-518 at the ultrasound probe 126.

The Twf may represent an interval for ultrasound signals to travel from the probe to the target sample and back to the probe 126 given the particular transmit focal point the wavefronts is curving towards. The arrival times are different for different receive MLA lines and the differences may be compensated radially to better align the recorded data for which the velocity field is calculated.

The controller circuit 102 compares the ultrasound data from the receive lines 202, 254, 302, 354, 402 with the correction times of the Twf for the corresponding transmit wavefronts 519-521 of the registration model 502. The controller circuit 102 shifts the recorded ultrasound data radially for the receive lines 202, 254, 302, 354, 402 based on the Twf in the registration model 502 to compensate for the curvature introduced by the curved wavefront. For example, the controller circuit 102 shifts the ultrasound data radially to compensate the transmit wavefronts 519-521 of the registration model 502 based on the Twf. The registration of the receive lines 202, 254, 302, 354, 402 enables the ultrasound data at the common positions within the ROI 201 to be aligned with each other.

For example, the receive line 202 includes two wavefronts 530, 531 representing the ultrasound data acquired along the receive line 202a. The controller circuit 102 compares a position of when the wavefronts 530, 531 were received with the transmit wavefronts 519-520 of the receive line 517. The controller circuit 102 registers the receive line 202 to form the registered receive line 202a. For example, the controller circuit 102 determines that the wavefront 530 is delayed relative to the wavefront 519 by ten microseconds. The controller circuit 102 shifts the data radially corresponding to the wavefront 530 by ten microseconds to match (e.g., occur at the same time) the wavefront 519 and form the wavefront 530a. In another example, the controller circuit 102 determines that the wavefront 531 is received earlier relative to the wavefront 520. The controller circuit 102 shifts the data radially corresponding to the wavefront 531 to match the receive line 517 of the registration model 502 to form the registered ultrasound data of the receive line 202a. For example, the controller circuit 102 shifts the wavefront 531 by ten microseconds to form the wavefront 531a.

The controller circuit 102 identifies speckle tracking from the ultrasound data based on the echoes received along the receive lines 202, 254, 302, 354, 402. The controller circuit 102 identifies velocity data from the speckle tracking, which represents displacement of blood particles identified in the ultrasound data between the repeated fire into each individual direction for the plurality of Tx beams. The controller circuit 102 estimates a velocity field from the velocity data. For example, the velocity field represents the changes in echoes (e.g., representing blood particles) identified in the receive lines 202, 254, 302, 354, 402 for the sectors 210-214. The controller circuit 102 forms the velocity field based on a pattern formed from the velocity data identified from the echoes. The pattern is based on the individual particles (e.g., the echoes) that move along velocities identified by the speckle tracking from the controller circuit 102. The pattern is displaced between the sectors 210-214 based on the ultrasound data acquired from the acquisition frames 200, 250, 300, 350, 400. The controller circuit 102 weights the velocity fields based on a weighting signal 602

Figure 4:
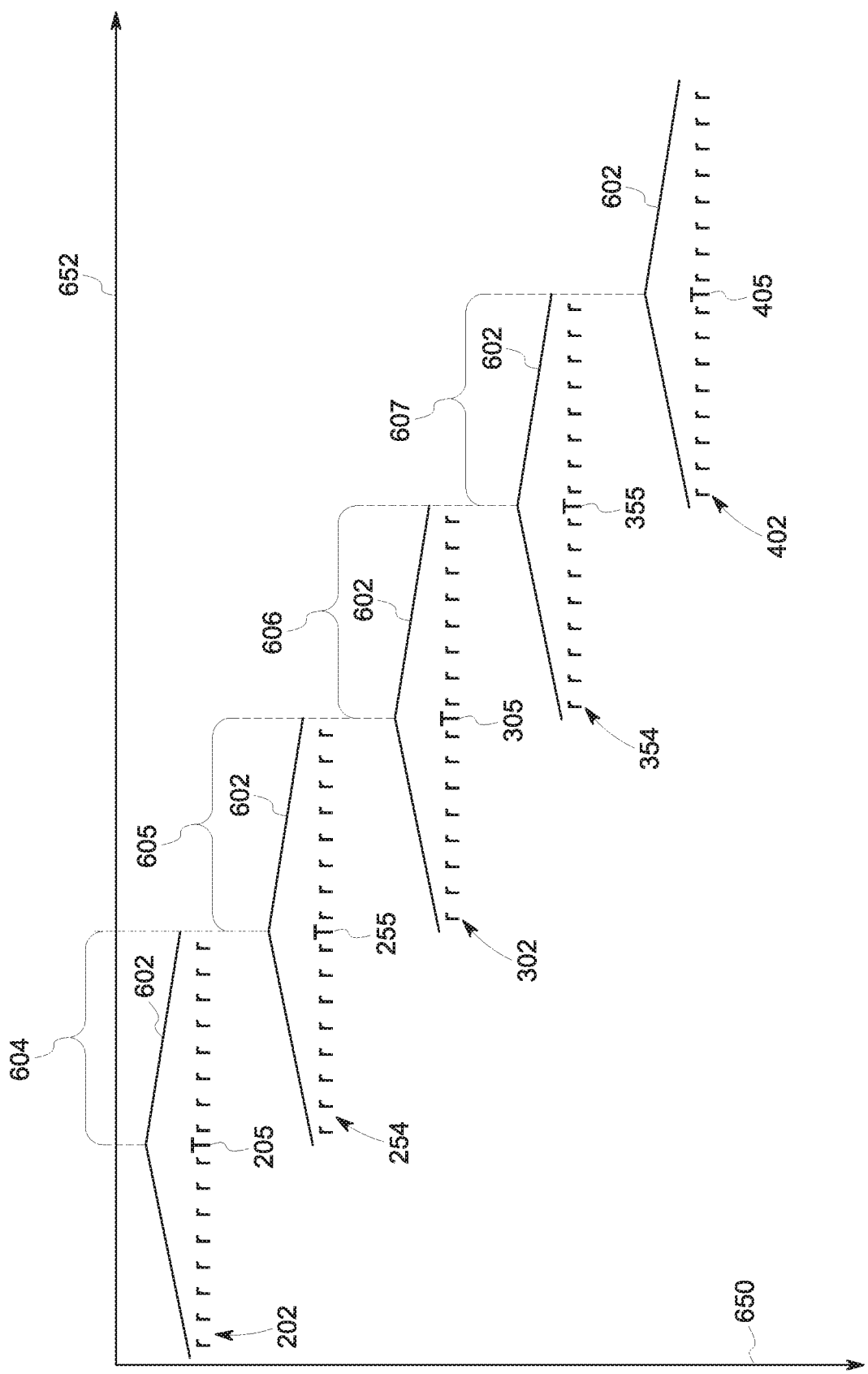
FIG. 4 illustrates an embodiment of a weighting signal relative to receive lines.

FIG. 4 illustrates an embodiment of the weighting signal 602 positioned relative to a portion of the receive lines 202, 254, 302, 354, 402. The receive lines 202, 254, 302, 354, 402 are shown over time along a vertical axis 650 based on when the at least two successive Tx beams 205, 255, 305, 355, 405 were fired from the ultrasound probe 126. The receive lines 202, 254, 302, 354, 402 are shifted along a horizontal axis 652 representing an angle relative to the ultrasound probe 126. For example, a position of the receive lines 202, 254, 302, 354, 402 along the axis 652 correspond to the different sectors 210-214, respectively.

The weighting signal 602 is shown as a linear weighting signal, which is centered at the transmit beam axes (e.g., 'T') of the at least two successive Tx beams 205, 252, 305, 352, 405. The ultrasound data received along the receive lines 202, 254, 302, 354, 402 is represented as 'r' in FIG. 4. Optionally, the weighting signal 602 may be parabolic, exponential, and/or the like centered at the transmit beam axes. Portions of the ultrasound data of the receive lines 202, 254, 302, 354, 402 overlap with each other representing the overlap regions 604-607 (e.g., which correspond to the overlap portions 206, 256, 306, 356, 406). For example, a portion of the ultrasound data of the receive lines 202 and 254 is within the overlap region 604, a portion of the ultrasound data of the receive lines 254 and 302 is within the overlap region 605, a portion of the ultrasound data of the receive lines 302 and 354 is within the overlap region 606, and a portion of the ultrasound data of the receive lines 354 and 402 is within the overlap region 607. The ultrasound data of the overlap regions 604-607 represent a portion of the receive lines 202, 254, 302, 354, 402 that are positioned within the weighting signals 602 of adjacent receive lines 202, 254, 302, 354, 402. The ultrasound data of the overlap regions 604-607 represent the one or more common spatial positions of the ROI 201 of another receive line 202, 254, 302, 354 402. The ultrasound data of the overlap regions 604-607 represent collinear ultrasound data. For example, the ultrasound data within the overlap regions 604-607 represents a common spatial position of the ROI 201 of the receive lines 202, 254, 302, 354, 402.

The controller circuit 102 weights the velocity fields based on the weighting signal 602. The weight applied by the controller circuit 102 is based on a distance from the corresponding transmit beam axes, which is represented as a position of the at least two successive Tx beams 205, 255, 305, 355, 405. The weights may represent a ratio based on a spatial distance of the ultrasound data, which corresponds to the velocity data forming the velocity fields from the transmit beam axes. The weight values represent a portion of the weight value applied to the velocity fields. For example only, the weight values may represent a ratio of ⅟₁₆, which is reduced based on distance from the transmit beam axis. For example, the receive lines 202, 254, 302, 354, 402 at a greater distance to the transmit beam axes should be weighted in the interpolated output less than receive lines 202, 254, 302, 354, 402 closer to the transmit beam axes with which they were recorded. It may be noted in various embodiments the weighted ratio may represent a higher resolution than 16 (e.g., 18, 20, 30) and/or a lower resolution than 16 (e.g., 6). The ultrasound data received along the receive lines 202, 254, 302, 354, 402 outside of the weighting signal 602 have a weight of zero. For example, the velocity fields based on ultrasound data outside of the weighting signal 602 is discarded by the controller circuit 102. The discarded ultrasound data is not included in the overlap regions 604-607. Based on the weighting signal 602, the controller circuit 102 forms weighted velocity fields The controller circuit 102 interpolates the weighted velocity fields at the common positions, which correspond to the different overlap regions 604-607. For example, the controller circuit 102 configures a proximity of the transmit beam axes relative to each other. The proximity of the transmit beam axes are configured by the controller circuit 102 such that at least a portion of the weighting signal 602 of the receive lines 202, 254, 302, 354, 402 overlap with each other at the overlap regions 604-607. For example, the controller circuit 102 configures the transmit beam axes to be within the weighting signal 602 of one or more alternative receive lines 202, 254, 302, 354, 402, respectively, to form the different overlap regions 604-607. The controller circuit 102 interpolates the overlap regions 604-607 separately. The controller circuit 102 interpolates the weighted velocity fields based on the weighting signal 602 and the receive lines 202, 254, 302, 354, 402. For example, the controller circuit 102 calculates a weighted mean for the overlap region 604 at the common location of the receive lines 202, 254. The weighted mean represents a mean of the velocities of the velocity fields at the common positions, for example, corresponding to the different overlap regions 604-607. For example, the controller circuit 102 calculates the weighted mean based on the weight signal 602 at the overlap region 604 of the weighted velocity fields, which adjusts the velocities (e.g., direction, magnitude) of the velocity field at the common location. The controller circuit 102 interpolates the remaining overlap regions 605-607, separately, by determining corresponding weighted means of the weighted velocity fields, which adjusts the weighted velocity fields at the common location. It may be noted that in various embodiments the controller circuit 102 may configure the transmit beam axes such that the overlap regions 604-607 do not overlap and/or transmit additional Tx beams to extend the overlap regions 604-607 with respect to each other along the receive lines 202, 254, 302, 354, 402.

Figure 5:
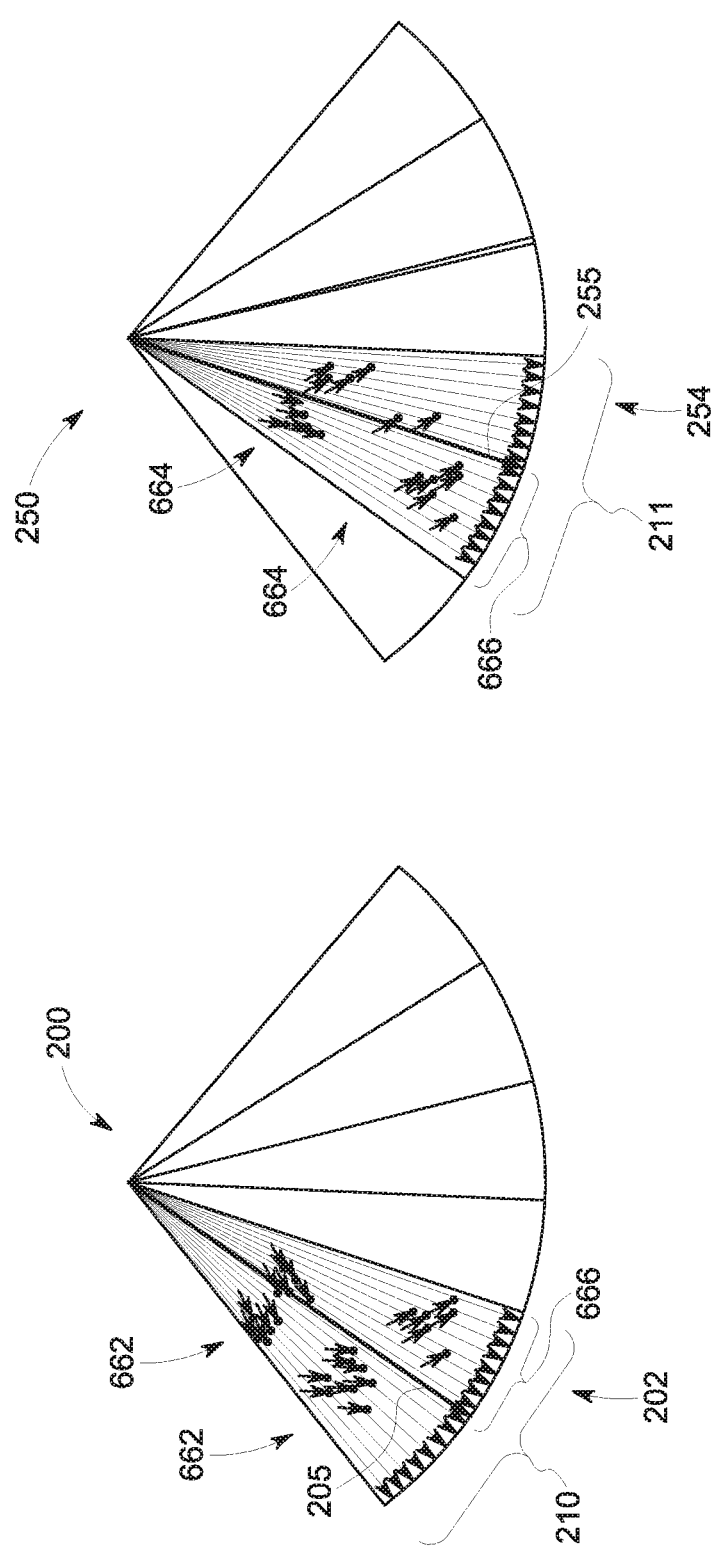
FIG. 5 illustrates an embodiment of velocity data based on a pair of acquisition frames.

FIG. 5 illustrates an embodiment of velocity data based on the acquisition frames 200, 250.

For example, the controller circuit 102 instructs the ultrasound probe 126 to transmit at least two successive Tx beams (e.g., the Tx beam 205) at the sector 210. The controller circuit 102 receives echoes 662 along the receive lines 202. The echoes 662 represent blood particles acquired from the at least two successive Tx beams 205 at the sector 210. The controller circuit 102 receives echoes 662 along the receive lines 202, which represent displacement of the blood particles based on time differences between the at least two successive Tx beams 205. Successively, the controller circuit 102 instructs the ultrasound probe 126 to transmit at least two successive Tx beams 255 at the sector 211. The controller circuit 102 receives echoes 664 along the receive lines 254. The echoes 664 represent blood particles acquired from the at least two successive Tx beams 255 at the sector 211. Based on a displacement of the echoes 664 from the time difference between the at least two successive Tx beams 255, the controller circuit 102 can determine velocity data. For example, the difference in position of the echoes 662, 664 within the sectors 210-211 represent the velocities of the speckle tracking 660. A portion 666 of the speckle tracking 660 is shown having a velocity having a downward and left motion. Additionally or alternatively, a portion 668 of the speckle tracking 660 is shown having a velocity having a downward and right motion. It may be noted that the controller circuit 102 may instruct additional Tx beams within the sectors 210-211 than the two Tx beams 205, 255 shown in FIG. 5.

A portion 666 of the velocity data from the receive lines 202, 255 overlap with each other, which corresponds to the overlap region 604 (FIG. 4). The interpolation between the Tx beams 205, 255 result in a spatially smooth estimate of the velocity field for the sectors 210-211.

Figure 6:
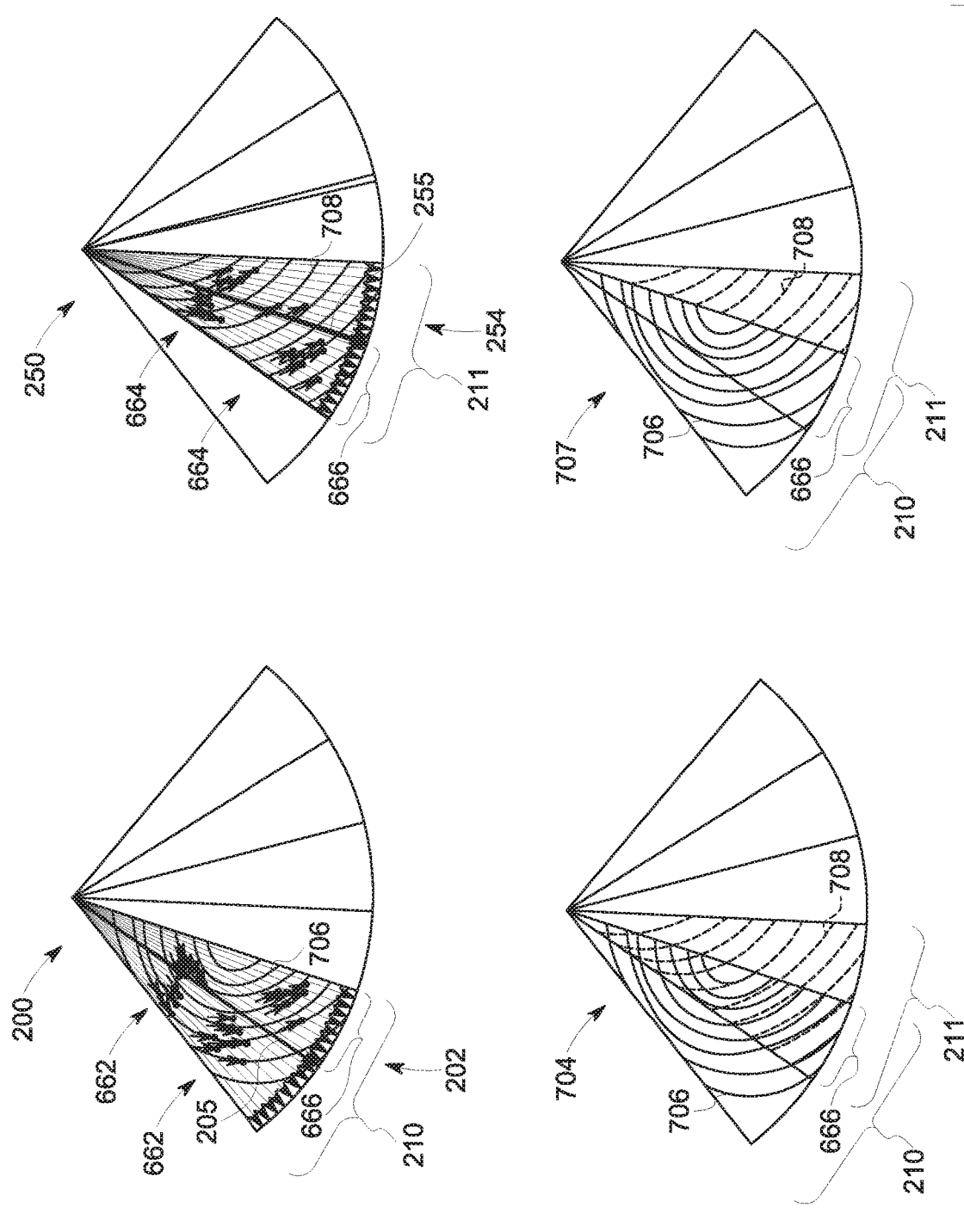
FIG. 6 illustrates an embodiment of velocity fields based on acquisition frames.

FIG. 6 further illustrates an embodiment of velocity fields 706, 708 based on the acquisition frames 200, 250. For example, the controller circuit 102 identifies the velocity data based on the echoes 662, 664 received during the acquisition frames 200, 250 corresponding to the sectors 210-211. In connection with FIG. 5, the controller circuit 102 determines velocity data from the ultrasound data received along the receive lines 202, 254. Based on velocity data the controller circuit 102 estimates the velocity fields 706, 708. For example, the velocity field 706 represents the changes in echoes 662 (e.g., representing blood particles) between the at least two successive Tx beams 205. The controller circuit 102 forms the velocity field 706 based on a pattern formed from the velocity data identified from the echoes 662. The pattern is based on the individual particles (e.g., the echoes 662) that move along velocities identified from the speckle tracking by the controller circuit 102. The pattern is displaced between the sectors 210-211 based on the overlap between the adjacent sectors 210-211. The pattern estimated by the controller circuit 102 is shown as the solid lines representing the velocity field 706. The controller circuit 102 continues the estimation for the velocity data for the remaining sectors 211-214. For example, the controller circuit 102 estimates the velocity field 708 based on the pattern formed from the echoes 664. For example, the velocity field 708 represents the change in echoes identified from the velocity data at the sector 211. It may be noted that the velocity fields 706, 708 are acquired at different times.

The velocity fields 704 acquired from the sectors 210-211 prior to interpolation by the controller circuit 102 includes a mismatch. There is a small transition between the velocity fields 706, 708 at the common position, which provides a mismatch. The transition occurs at the common position between the sectors 210-211, at the portion 666 and/or overlap region 604. The controller circuit 102 avoids discontinuities by estimating a velocity field from two overlapping adjacent sectors 210-211 that overlap (e.g., the sectors 210-211, the sectors 211-212). Additionally or alternatively, the controller circuit 102 may set up an overlap between more than two adjacent sectors to interpolate and thus avoid discontinuities of a velocity field. The controller circuit 102 may form a velocity field 706, 708 based on the ultrasound data acquired within the sectors 210-211.

For example, the controller circuit 102 interpolates (e.g., calculation of the mean) the overlap region 604 (e.g., the portion 666), which results in a continuous change in the velocity field over time between the Tx beams 205, 255. Additionally, the interpolation improves the estimate of the velocity field at the common positions (e.g., the portion 666) and decreases noise or uncertainty of the weighted velocity data.

The controller circuit 102 interpolates the weighted velocity fields 704 data within the portion 666 or the overlap region 604 by calculating a weighted mean (e.g., arithmetic mean, geometric mean) of the weighted velocity fields 704. For example, the controller circuit 102 calculates the weighted mean of the overlap region 604 (e.g., corresponding to the portion 666) of the weighted velocity fields 704 acquired along the receive lines 202, 254. The interpolation of the weighted velocity fields 704 of the overlap region 604 provides recordings of the velocity field at different instances in time.

The velocity field 707 includes the interpolation of the weighted velocity data at the common position (e.g., the portion 666, the overlap region 604). The controller circuit 102 interpolates the velocity data at the portion 666 and/or the overlap region 604, which adjusts a portion of the velocity fields 706, 708. For example, the interpolation by the controller circuit 102 provides a smoother transition between the velocity fields 706, 708 acquired at the different sectors 210-211. The additional velocity data at the portion 666 improves the estimate and decreases noise of the velocity field. The interpolation of the velocity fields in the overlap region provides lateral continuity of the velocity fields from the interpolation.

Returning to FIG. 1, the controller circuit 102 may be operably coupled to and/or control a communication circuit 104. The communication circuit 104 is configured to receive and/or transmit information with one or more alternative medical imaging systems, a remote server, and/or the like along a uni-directional and/or bi-directional communication link. The remote server may represent a database that includes patient information, the registration model 502 of the ROI 201, remotely stored ultrasound images of a patient, and/or the like. The communication circuit 104 may represent hardware that is used to transmit and/or receive data along the uni-directional and/or bi-directional communication link. The communication circuit 104 may include a transceiver, receiver, transceiver and/or the like and associated circuitry (e.g., antennas) for wired and/or wirelessly communicating (e.g., transmitting and/or receiving) with the one or more alternative medical imaging systems, the remote server, and/or the like. For example, protocol firmware for transmitting and/or receiving data along the uni-directional and/or bi-directional communication link may be stored in the memory 106, which is accessed by the controller circuit 102. The protocol firmware provides the network protocol syntax for the controller circuit 102 to assemble data packets, establish and/or partition data received along the bi-directional communication links, and/or the like.

The uni-directional and/or bi-directional communication links may be a wired (e.g., via a physical conductor) and/or wireless communication (e.g., utilizing radio frequency (RF)) link for exchanging data (e.g., data packets) between the one or more alternative medical imaging systems, the remote server, and/or the like. The bi-directional communication links may be based on a customized communication protocol and/or a standard communication protocol, such as Ethernet, TCP/IP, Wi-Fi, 802.11, Bluetooth, and/or the like.

The controller circuit 102 is operably coupled to the display 138 and the user interface 142. The display 138 may include one or more liquid crystal displays (e.g., light emitting diode (LED) backlight), organic light emitting diode (OLED) displays, plasma displays, CRT displays, and/or the like. The display 138 may display patient information, one or more ultrasound images and/or videos, components of a graphical user interface, one or more 2D, 3D, or 4D ultrasound image data sets from ultrasound data stored in the memory 106 or currently being acquired in real-time, anatomical measurements, diagnosis, treatment information, tags, and/or the like received by the display 138 from the controller circuit 102.

The user interface 142 controls operations of the controller circuit 102 and the medical imaging system 100. The user interface 142 is configured to receive inputs from the clinician and/or operator of the medical imaging system 100. The user interface 142 may include a keyboard, a mouse, a touchpad, one or more physical buttons, and/or the like. Optionally, the display 138 may be a touch screen display, which includes at least a portion of the user interface 142. For example, a portion of the user interface 142 may correspond to a graphical user interface (GUI) generated by the controller circuit 102, which is shown on the display 138. The touch screen display can detect a presence of a touch from the operator on the display 138 and can also identify a location of the touch with respect to a surface area of the display 138. For example, the user may select one or more user interface components of the GUI shown on the display by touching or making contact with the display 138. The user interface components may correspond to graphical icons, textual boxes, menu bars, and/or the like shown on the display 138. The user interface components may be selected, manipulated, utilized, interacted with, and/or the like by the clinician to instruct the controller circuit 102 to perform one or more operations as described herein. The touch may be applied by, for example, at least one of an individual's hand, glove, stylus, and/or the like.

The memory 106 includes parameters, algorithms, protocols of one or more ultrasound exams, data values, and/or the like utilized by the controller circuit 102 to perform one or more operations described herein. The memory 106 may be a tangible and non-transitory computer readable medium such as flash memory, RAM, ROM, EEPROM, and/or the like.

The ultrasound probe 126 may have a transmitter 122, transmit beamformer 121 and probe/SAP electronics 110. The probe/SAP electronics 110 may be used to control the switching of the transducer elements 124. The probe/SAP electronics 110 may also be used to group transducer elements 124 into one or more sub-apertures. The ultrasound probe 126 may be configured to acquire ultrasound data or information from the anatomical structure of the patient. The ultrasound probe 126 is communicatively coupled to the controller circuit 102 via the transmitter 122. The transmitter 122 transmits a signal to a transmit beamformer 121 based on acquisition settings received by the controller circuit 102. The acquisition settings may define an amplitude, pulse width, frequency, gain setting, scan angle, power, time gain compensation (TGC), resolution, and/or the like of the ultrasonic pulses emitted by the transducer elements 124. The transducer elements 124 emit pulsed ultrasonic signals into the patient (e.g., a body). The acquisition settings may be defined by the user operating the user interface 142. The signal transmitted by the transmitter 122 in turn drives a plurality of transducer elements 124 within the transducer array 112.

The transducer elements 124 emit pulsed ultrasonic signals into a body (e.g., patient) or volume corresponding to the acquisition settings along one or more scan planes. The ultrasonic signals may include, for example, one or more reference pulses, imaging pulses, one or more pushing pulses (e.g., shear-waves), and/or the like. At least a portion of the pulsed ultrasonic signals backscatter from the ROI 201 to produce echoes. The echoes are delayed in time and/or frequency according to a depth or movement, and are received by the transducer elements 124 within the transducer array 112. The ultrasonic signals may be used for imaging, for measuring changes in position or velocity within the ROI 201, and/or for therapy, among other uses.

The transducer elements 124 convert the received echo signals into electrical signals, which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored in memory 106, temporarily. The digitized signals correspond to the backscattered waves received by each transducer element 124 at various times. After digitization, the signals still may preserve the amplitude, frequency, phase information of the backscatter waves.

Optionally, the controller circuit 102 may retrieve the digitized signals stored in the memory 106 to prepare for the beamformer processor 130. For example, the controller circuit 102 may convert the digitized signals to baseband signals or compressing the digitized signals.

The beamformer processor 130 may include one or more processors. Optionally, the beamformer processor 130 may include a central processing unit (CPU), a graphic processing unit capable of doing calculations (GPU), one or more microprocessors, or any other electronic component capable of processing inputted data according to specific logical instructions. Additionally or alternatively, the beamformer processor 130 may execute instructions stored on a tangible and non-transitory computer readable medium (e.g., the memory 106) for beamforming calculations using any suitable beamforming method such as adaptive beamforming, synthetic transmit focus, aberration correction, synthetic aperture, clutter reduction and/or adaptive noise control, and/or the like. Optionally, the beamformer processor 130 may be integrated with and/or a part of the controller circuit 102. For example, the operations described as being performed by the beamformer processor 130 may be configured to be performed by the controller circuit 102.

The beamformer processor 130 performs beamforming on the digitized signals of transducer elements and outputs a radio frequency (RF) signal. The RF signal is then provided to an RF processor 132 that processes the RF signal. The RF processor 132 may include one or more processors. Optionally, the RF processor 132 may include a central processing unit (CPU), a graphics processing unit (GPU), one or more microprocessors, or any other electronic component capable of processing inputted data according to specific logical instructions. Additionally or alternatively, the RF processor 132 may execute instructions stored on a tangible and non-transitory computer readable medium (e.g., the memory 106). Optionally, the RF processor 132 may be integrated with and/or a part of the controller circuit 102. For example, the operations described as being performed by the RF processor 132 may be configured to be performed by the controller circuit 102. Optionally the RF data received by the individual probe transducer elements or sub aperture processors may go through the RF processor 132 that mixes and bandpass filters the RF data in order to produce in-phase/quadrature (IQ) data prior to the beamforming, beamforming subsequently being performed on these band limited data.

The RF processor 132 may generate different ultrasound imaging data types and/or modes (e.g., B-mode, C-mode, M-mode, speckle tracking, color Doppler (e.g., color flow, velocity/power/variance), tissue Doppler) for multiple scan planes or different scanning patterns based on the predetermined settings of the first model. For example, the RF processor 132 may generate tissue Doppler data for multi-scan planes. The RF processor 132 gathers the information (e.g., IQ, B-mode, speckle tracking, color Doppler, tissue Doppler, and Doppler energy information) related to multiple data slices and stores the data information, which may include time stamp and orientation/rotation information, in the memory 106.

Alternatively, the RF processor 132 may include a complex demodulator (not shown) that demodulates the RF signal to form IQ data pairs representative of the echo signals. The RF or IQ signal data may then be provided directly to the memory 106 for storage (e.g., temporary storage). Optionally, the output of the beamformer processor 130 may be passed directly to the controller circuit 102. Additionally or alternatively, the RF processor 132 may be in front of the beamformer processor 130, demodulating the channel data from each element or sub aperture to form IQ data pairs that are beamformed and subsequently processed further into B-mode representation, color flow data or Doppler trace data.

The controller circuit 102 may be configured to process the acquired ultrasound data (e.g., RF signal data or IQ data pairs) and prepare and/or generate frames of ultrasound image data representing the anatomical structure for display on the display 138. Acquired ultrasound data may be processed in real-time by the controller circuit 102 during the ultrasound exam as the echo signals are received. Additionally or alternatively, the ultrasound data may be stored temporarily in the memory 106 during the ultrasound exam and processed in less than real-time in a live or off-line operation.

The memory 106 may be used for storing processed frames of acquired ultrasound data that are not scheduled to be displayed immediately or to store post-processed images, firmware or software corresponding to, for example, a graphical user interface, one or more default image display settings, programmed instructions, and/or the like. The memory 106 may store the ultrasound images such as 3D ultrasound image data sets of the ultrasound data, where such 3D ultrasound image data sets are accessed to present 2D and 3D images. For example, a 3D ultrasound image data set may be mapped into the corresponding memory 106, as well as one or more reference planes. The processing of the ultrasound data, including the ultrasound image data sets, may be based in part on user inputs, for example, user selections received at the user interface 142.

Figure 7:
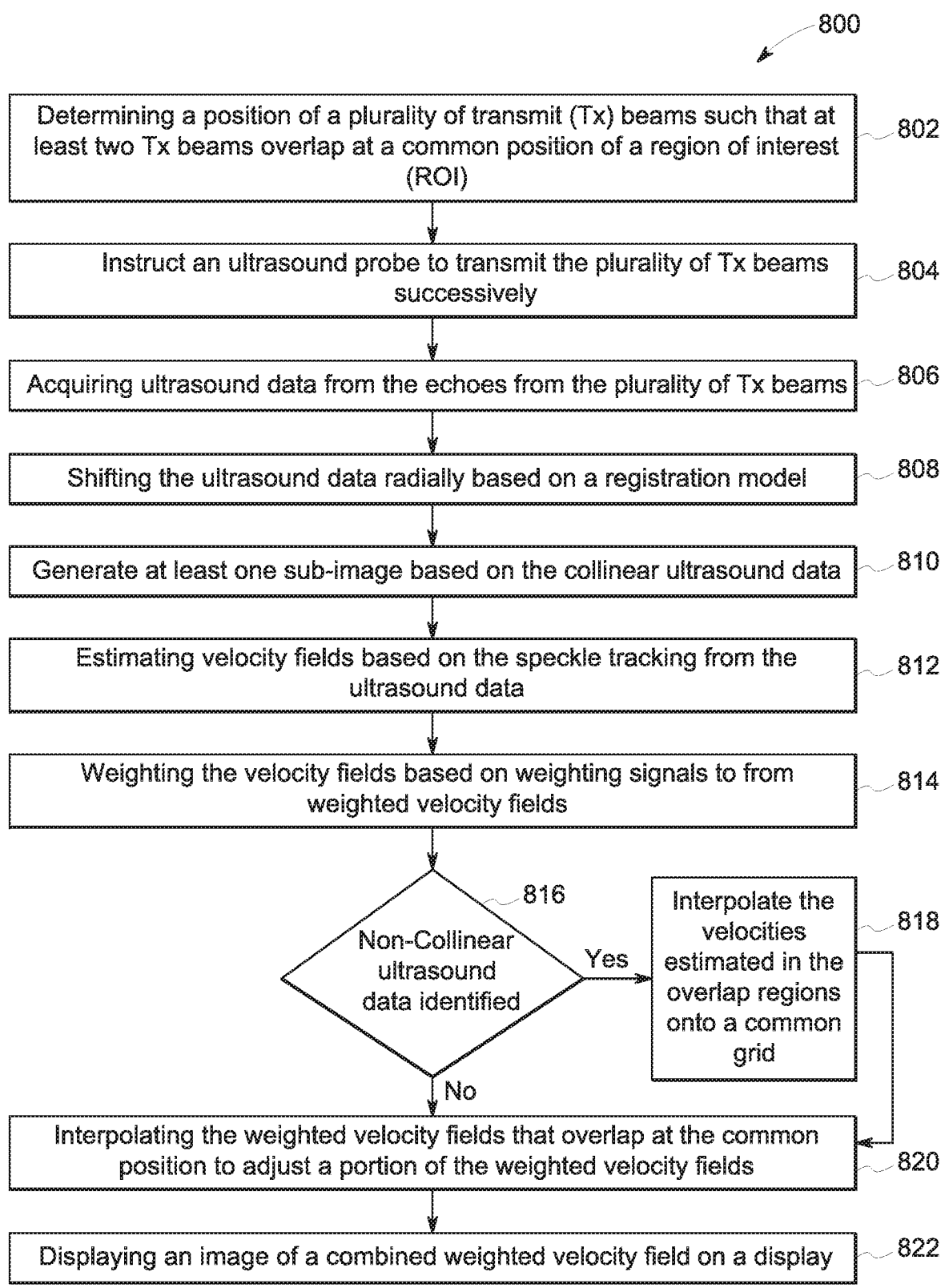
FIG. 7 illustrates a flow chart of an embodiment of a method for speckle imaging.

FIG. 7 illustrates a flow chart of an embodiment of a method for speckle imaging, in accordance with an embodiment herein. The method 800, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. It may be noted that the steps described of the method 800 may be performed during the ultrasound exam in real-time. In various embodiments, portions, aspects, and/or variations of the method 800 may be used as one or more algorithms to direct hardware to perform one or more operations described herein.

Beginning at 802, the controller circuit 102 determines a position of a plurality of Tx beams (e.g., the Tx beams 205, 255, 305, 355, 405, 455 of FIG. 2). For example, the controller circuit 102 may configure the plurality of Tx beams such that at least two successive Tx beams 205, 255, 305, 355, 405 are positioned within each sector 210-214. Based on the orientation of the sectors 210-214, at least one sector 210-214 overlaps at least one adjacent sector 210-214 at one or more common positions. For example, the at least two successive Tx beams 205, 255 are fired within the sectors 210-211, respectively, resulting in the receive lines 202, 254. The receive lines 202, 254 include a portion 666 (FIGS. 5-6) that overlap with each other at the common position. The ultrasound data acquired at the portion 666 is represented as the overlap region 604 shown in FIG. 4. Optionally, more than two successive Tx beams may be transmitted in each of the sectors 210-214.

Figure 8:
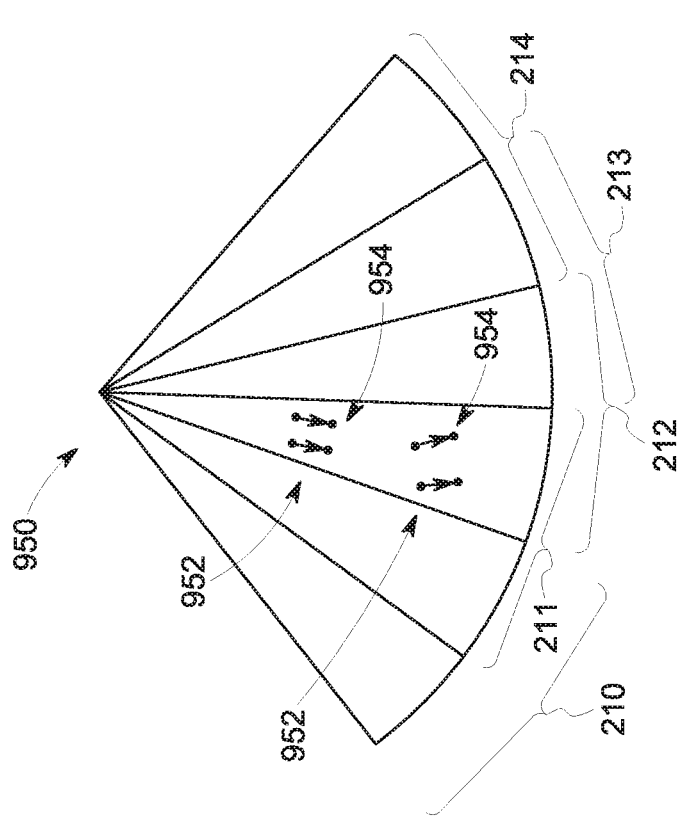
FIG. 8 illustrate an embodiment of at least one sub-image based on non-collinear ultrasound data.
Figure 8:
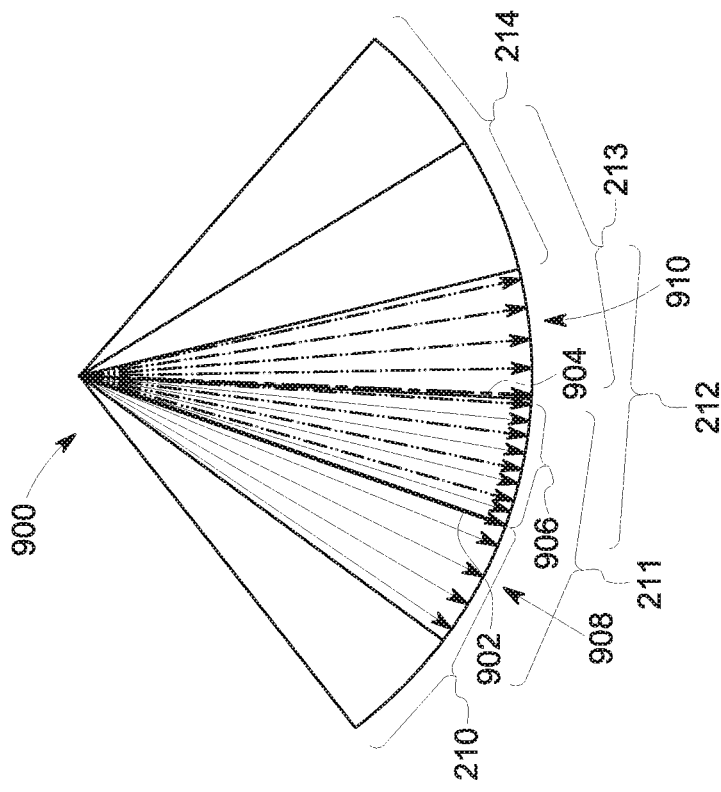

The common position is based on an overlap position of the transmit beam axis with respect to the sectors 210-214, which form the overlap regions 604-607. For example, the controller circuit 102 fires and/or transmits the plurality of Tx beams within sectors 210-214 that are configured such that the receive lines 202, 254, 302, 354, 402 overlap with each other. Additionally or alternatively as shown in FIG. 4, the controller circuit 102 may configure the plurality of Tx beams such that a distance between the transmit beam axes is less than the weighting signal 602. For example, the weighting signal 602 is centered at the transmit beam axes corresponding to the position of the plurality of Tx beams within the sectors 210-214. For example, the controller circuit 102 may adjust positions of the plurality of Tx beams to extend a length of the overlap regions 604-607 along the receive lines 202, 254, 302, 354, 402. Additionally or alternatively, the receive lines may be configured to not be collinear from one section to the next (e.g., the receive beams need not be defined in exactly the same location in each of the sections as long as the spatial area they span out is overlapping). FIG. 8 illustrate an embodiment of at least one sub-image 950 based on non-collinear ultrasound data 900. For example, the controller circuit 102 configures Tx beams 902, 904 transmitted from the ultrasound probe within the sector 212 to be displaced with respect to each other. The Tx beams 902, 904 are positioned at opposing sides of the sector 212. The Tx beam 902 receives echoes from a receive line 908, and the Tx beam 904 received echoes from a receive line 910. There is an overlap 906 of the receive lines 908, 910. For example, a spatial extension of the Tx beam 902 overlaps with a spatial extension of the Tx beam 904 corresponding to the overlap 906. The controller circuit 102 can define a velocity field at the overlap 906. For example, the controller circuit 102 calculates within the sector 212 a common grid along radial beams or in Cartesian pixels at which a velocity can be procured by interpolation of the velocity field. The controller circuit 102 identifies echoes 952 representing blood particles (e.g., speckle tracking) based on the Tx beam 902, and echoes 954 representing blood particles based on the Tx beam 904. The adjustment in the echoes 952, 954 identified by the controller ciruct 102 forms the velocity field, which is shown in the sub-image 950. It may be noted that the controller circuit 102 may be configured such that more than two Tx beams of the plurality of Tx beams do not have overlapping receive lines.

At 804, the controller circuit 102 instructs the ultrasound probe 126 to transmit the plurality of Tx beams successively with respect to each other. For example, the controller circuit 102 may instruct the transmitter 122 to successively transmit the at least two successive Tx beams 205, 255, 305, 355, 405 within the sectors 210-214. The controller circuit 102 acquires speckle tracking data from the receive lines 202, 254, 302, 354, 402. For example, when the at least two successive Tx beams 205 are fired and/or transmitted by the ultrasound probe 126 within the sector 210, and the ultrasound data is acquired from the receive lines 202. After the at least two successive Tx beams 205, the ultrasound probe 126 fires and/or transmits the at least two successive Tx beams 255 within the sector 211, and the ultrasound data is acquired from the receive lines 254 for speckle tracking. It may be noted that the Tx beams 205, 255 overlap with each other at a common position within the sector 210 (as shown in FIGS. 2B and 4). Optionally, the controller circuit 102 may instruct more than two Tx beams for each of the sectors 210-215. For example, the controller circuit 102 may repeat the process a set number of times (e.g., M times) for each of the sectors 210-215.

At 806, the controller circuit 102 acquires ultrasound data from the echoes from the plurality of Tx beams. For example, the transducer array 112 receives the ultrasound data along the receive lines 202, 254, 302, 354, 402. The ultrasound data may be stored in the memory 106 after being processed by the controller circuit 102, the beamformer processor 130, the RF processor 132, and/or the like.

At 808, the controller circuit 102 shifts the ultrasound data radially based on a registration model (e.g., similar to the registration model 502). For example, a distance between the receive lines 202, 254, 302, 354, 402 and the Tx beams 205, 255, 305, 355, 405 may give rise to a slight misregistration of the location of the echoes (e.g., blood particles) in different parts of the sectors 210-214. The misregistration is based on where the transmit beam axes is located, and is due to the different arrival times of the curved transmitted wavefront at the particular receive points at the ROI 201. The registration model is configured to correct for the misregistration. The controller circuit 102 corrects the ultrasound data radially based on the registration model to improve the accuracy of the velocity estimates from the speckle tracking data. It may be noted that the correction by the controller circuit 102 may occur after and/or during receive beamforming (e.g., prior to speckle tracking data acquisition). The correction by the controller circuit 102 ensures that the interpolation of multiple estimates of the velocity field described herein is optimally aligned and have as little discrepancy as possible.

The correction by the controller circuit 102 represents a temporal shift and/or compensation on when the ultrasound data is received along the receive lines 202, 254, 302, 354, 402, 454. The registration model includes estimations on when ultrasound data along the receive lines 202, 254, 302, 354, 402, 454 will be received by the ultrasound probe 126. Optionally, the memory may include multiple registration models. For example, a depth and/or difference in position of the ROI 201 between the different sectors 210-215 can be represented as different registration models. The memory 106 may include a first registration model based on the depth and/or position of the ROI 201 of the sector 210, and a second registration model based on the depth and/or position of the ROI 201 of the sector 211

For example, the controller circuit 102 compares the one or more baseline wavefronts of the receive lines 202 with the registration model. The one or more wavefronts are indicative of the ultrasound data received along the receive lines 202. The controller circuit 102 compares when the one or more wavefronts were received along the receive lines 202 with the one or more wavefronts defined by the registration model. Based on the differences with the baseline wavefronts, the controller circuit 102 adjusts the one or more wavefronts of the receive lines 202 to match the one or more baseline wavefronts of the first registration model.

At 810, the controller circuit 102 generates at least one sub-image based on the collinear ultrasound data. For example, the collinear ultrasound data corresponds to the overlap regions 604-607 (FIG. 4) representing the common locations of the sectors 210-214. The sub-image is formed by the controller circuit 102 of the velocity data of the overlap of the sectors 210-214. For example, the controller circuit 102 identifies velocity data based on the speckle tracking of the ultrasound data acquired by the receive lines 202, 254, 302, 354, 402 for the overlap regions 604-607. Additionally or alternatively, the controller circuit 102 may generate first and second sub-images. The first and second sub-image may represent alternating sectors 210-214. For example, the velocity data of the overlap regions 604-607 that form the first and second sub-images. For example, the first sub-image includes the such that the velocity data. For example, the controller circuit 102 may form the first sub- At 812, the controller circuit 102 estimates velocity fields based on the speckle tracking from the ultrasound data. In connection with FIG. 6, the controller circuit 102 identifies velocities based on the echoes received during the acquisition frames 200, 250 corresponding to the sectors 210-211. The velocities form velocity fields 706, 708. For example, the velocity field 706 represents the changes in echoes (e.g., representing blood particles) identified from the receive lines 202 (FIG. 2) for the sector 210. The controller circuit 102 forms the velocity field 706 based on a pattern formed from the velocities identified from the echoes. The pattern is based on the individual particles (e.g., the echoes) that move along velocities identified for the speckle tracking by the controller circuit 102. The pattern is displaced between the sector 210 based on the ultrasound data acquired from the at least two successive Tx beams 205. The pattern is shown as the solid lines representing the velocity field 706. Additionally or alternatively, the controller circuit 102 identifies additional velocity fields for the acquisition frames 250, 300, 350, 400 corresponding to the sectors 211-214. For example, the controller circuit 102 may repeat the process for the plurality of successive Tx beams 255, 305, 355, 405 occurring within the sectors 211-214.

At 814, the controller circuit 102 weights the velocity fields based on the weighting signals (e.g., the weighting signals 602 FIG. 6) to form the weighted velocity fields. In connection with FIG. 4, the controller circuit 102 illustrates an embodiment of the weighting signal 602 of a portion of the receive lines 202, 254, 302, 354, 402 of the at least two successive Tx beams 205, 255, 305, 355, 405. The controller circuit 102 configured the at least two successive Tx beams 205, 255, 305, 355, 405 such that a portion of the receive lines 202, 254, 302, 354, 402, respectively, overlap with each other relative to the weighting signal 602. The weighting signal 602 is centered at the corresponding transmit beam axes. The transmit beam axes corresponds to a position of the at least two successive Tx beams 205, 255, 305, 355, 405 with respect to the sectors 210-214. The controller circuit 102 weights the velocity fields based on a position of the ultrasound data with respect to the weighting signal 602. For example, the weighting signal 602 may represent a ratio based on a spatial distance of the receive lines 202, 254, 302, 354, 402 from the transmit beam axes. The controller circuit 102 applies the ratio to the velocity fields based on a position of the ultrasound data acquired along the receive lines 202, 254, 302, 354, 402 with respect to the weighting signal 602.

At 816, the controller circuit 102 identifies non-collinear ultrasound data. The controller circuit 102 identifies the collinear ultrasound data based on positions of the plurality of Tx beams. In connection with FIG. 8, the controller circuit 102 determines that the Tx beams 902, 904 do not overlap at a common position. For example, the controller circuit 102 determines that the position of the Tx beams 902, 904 are at opposing positions within the sector 212, which do not overlap at any point within the sector 212. Based on the position of the Tx beams 902, 904, the controller circuit 102 identifies the ultrasound data acquired along the receive lines 908, 910 represent non-collinear ultrasound data.

If non-collinear ultrasound data is identified, then at 818, the controller circuit 102 interpolates velocities estimated in the overlap regions onto a common grid. For example, there is an overlap 906 of the receive lines 908, 910 from the Tx beams 902, 904. The controller circuit 102 can define a velocity field at the overlap 906. For example, the controller circuit 102 calculates within the sector 212 a common grid along radial beams or in Cartesian pixels at which a velocity can be procured by interpolation of the velocity field. The common grid may be aligned with the velocity fields from the at least two successive Tx beams 205, 255, 305. The controller circuit 102 adjusts the velocity fields within the sector 212 based on the measured velocities from the non-collinear ultrasound data.

Additionally or alternatively, the plurality of Tx beams may not include collinear ultrasound data. For example, the controller circuit 102 may configured the plurality of Tx beams such that there is no overlap to form only non-collinear ultrasound data. The plurality of Tx beams are directed to a common ROI 201, but do not acquire ultrasound data at a common position. For example, the regions covered by the MLA group of a first Tx beam overlaps with the region covered by the MLA group of a second (e.g., and/or more) Tx beams, even though the individual MLA lines are not exactly aligned. The controller circuit 102 determines a sub-sample accuracy for the non-collinear ultrasound data acquired by the plurality of Tx beams. For example, the controller circuit 102 generates the sub-images based on the plurality of Tx beams at overlap regions of the receive lines. The controller circuit 102 interpolates gaps positioned between receive lines of the successive plurality of Tx beams. For example, the controller circuit 102 determines a velocity field based on the non-collinear ultrasound data. The controller circuit 102 interpolate in time the receive lines across and between the plurality of Tx beams, which represent the gaps. For example, gaps between the receive lines are interpolated in time by the controller circuit 102. The controller circuit 102 by calculating a mean of the proximate non-collinear ultrasound data across and between the different receive lines to form the velocity field.

At 820, the controller circuit 102 interpolates the weighted velocity fields at the common position (e.g., the overlap regions 604-606 of FIG. 4) to adjust a portion of the velocity fields. The controller circuit 102 interpolates the weighted velocity fields within the overlap regions 604-607, individually. For example, the controller circuit 102 calculates the weighted mean (e.g., arithmetic mean, geometric mean) of the weighted ultrasound data of the receive lines 202, 254, 302, 354, 402 within the different overlap regions 604-607. For example, the controller circuit 102 calculates the mean of the weighted ultrasound data within the overlap region 604. The weighted mean calculated by the controller circuit 102 represents the interpolation of the weighted velocity fields based on the receive lines 202, 254. For example, the weighted mean represents the arithmetic mean, the geometric mean, and/or the like of the weighted ultrasound values of the receive lines 202, 254 of the overlap region 602. In connection with FIG. 6, based on the interpolation, the portion 666 of the velocity fields are adjusted.

Figure 9:
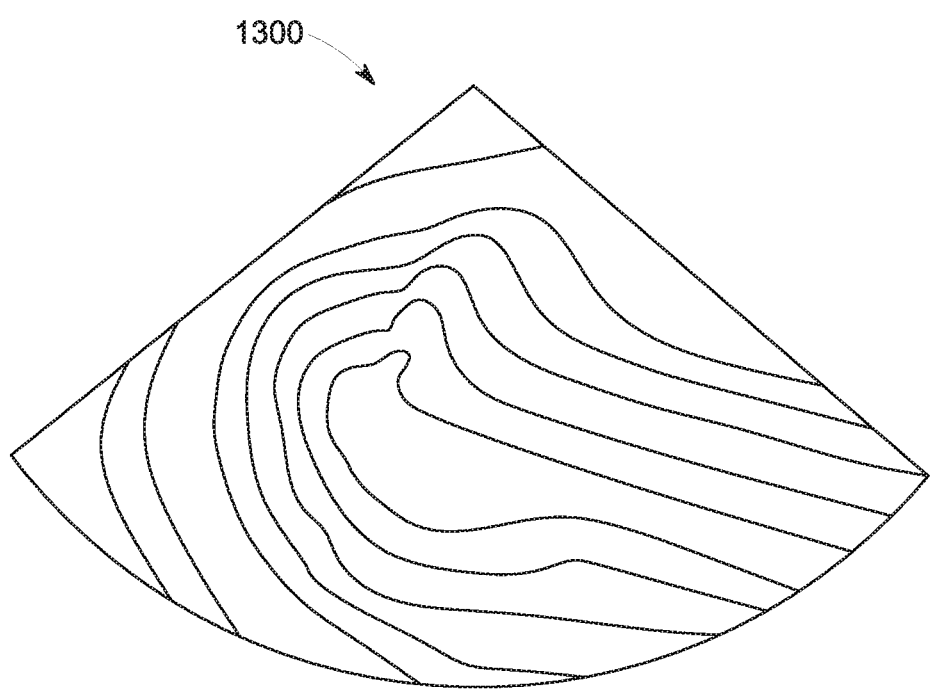
FIG. 9 illustrates an embodiment of an ultrasound image shown on a display.

At 822, the controller circuit 102 generates an image 1300 of a combined weighted velocity field on the display 138. FIG. 9 illustrates an embodiment of the image 1300 shown on the display 138. For example, the controller circuit 102 combines the different velocity fields corresponding to the sectors 210-214. The controller circuit 102 interpolates the overlap regions such that the combined velocity fields is continuous.

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, circuit, processor, or computer that is "configured to" perform a task or operation may be understood as being particularly structured to perform the task or operation (e.g., having one or more programs or Instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms ' software' and "firmware" are interchangeable, and include any computer program stored in memory for execution by a computer including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A computer implemented method, comprising:
   transmitting a plurality of transmit (Tx) beams from an ultrasound probe into each sector of multiple sectors of a scan region that includes a region of interest (ROI), wherein the plurality of Tx beams into each sector are transmitted successively with respect to each other, the plurality of Tx beams are configured to acquire ultrasound data along receive lines by repeatedly firing the Tx beams into the respective sector along a transmit beam axis, at least a first sector of the sectors and a second sector of the sectors overlap each other at an overlapping portion;
   performing speckle tracking for each sector by analyzing the ultrasound data acquired along the receive lines to calculate velocity data that represents movement of blood particles within the ROI, wherein the velocity data is calculated based on displacement of the blood particles identified in the ultrasound data acquired in response to successive Tx beams into the respective sector;
   estimating a velocity field for each sector of the multiple sectors based on the velocity data calculated via the speckle tracking;

weighting the velocity field for each sector based on distances of the receive lines from the transmit beam axis to form weighted velocity fields;

interpolating the weighted velocity field of the first sector within the overlapping portion and the weighted velocity field of the second sector within the overlapping portion to adjust the weighted velocity fields of the first sector and the second sector; and generating an image of a combined velocity field on a display by combining the weighted velocity fields, including the weighted velocity fields that are adjusted.

2. The computer implemented method of claim 1, further comprising identifying non-collinear ultrasound data from the ultrasound data, and generating at least one sub-image from the non-collinear ultrasound data.

3. The computer implemented method of claim 1, wherein weighting the velocity field for each sector comprises applying a weighting signal that is linear and is centered about the transmit beam axis of the plurality of Tx beams transmitted into the sector.

4. The computer implemented method of claim 1, wherein the interpolating operation includes calculating a weighted mean of the weighted velocity fields within the overlapping portion, and the weighted velocity fields are combined such that the image of the combined velocity field on the display is continuous.

5. The computer implemented method of claim 1, further comprising shifting the ultrasound data radially based on a registration model independently for each of the plurality of Tx beams.

6. The computer implemented method of claim 1, further comprising determining a position of a second transmit beam axis of a second Tx beam from the plurality of Tx beams relative to a first transmit beam axis of a first Tx beam from the plurality of Tx beams such that portions of the first and second Tx beams overlap at the overlapping portion.

7. The computer implemented method of claim 1, wherein the velocity field for each sector comprises a speckle pattern of velocities indicating the movement of the blood particles within the ROI.

8. The computer implemented method of claim 1, further comprising applying clutter filtering to sub-images generated from the ultrasound data.

9. The computer implemented method of claim 1, wherein weighting the velocity field for each sector comprises assigning less weight to the velocity data calculated via the speckle tracking by analyzing the ultrasound data received along a first receive line of the receive lines than the weight assigned to the velocity data calculated via the speckle tracking by analyzing the ultrasound data received along a second receive line of the receive lines which is closer than the first receive line to the transmit beam axis of the plurality of Tx beams transmitted into the sector.

10. The computer implemented method of claim 1, wherein the interpolating operation comprises calculating a mean between weighted velocity data from the weighted velocity field of the first sector based on the ultrasound data received along a first receive line and weighted velocity data from the weighted velocity field of the second sector based on the ultrasound data received along a second receive line, wherein the first and second receive lines are collinear and within the overlapping portion.

11. A medical imaging system, comprising:
an ultrasound probe configured to acquire ultrasound data;
a display; and
a controller circuit configured to:
instruct the ultrasound probe to transmit a plurality of transmit (Tx) beams into each sector of multiple sectors of a scan region that includes a region of interest (ROI), wherein the plurality of Tx beams into each sector are transmitted successively with respect to each other, the plurality of Tx beams are configured to acquire the ultrasound data along receive lines by repeatedly firing the Tx beams along a transmit beam axis, at least a first sector of the sectors and a second sector of the sectors overlap each other at an overlapping portion;
perform speckle tracking for each sector by analyzing the ultrasound data acquired along the receive lines to calculate velocity data that represents movement of blood particles within the ROI, wherein the velocity data is calculated based on displacement of the blood particles identified in the ultrasound data acquired in response to successive Tx beams into the respective sector;
estimate a velocity field for each sector of the multiple sectors based on the velocity data calculated via the speckle tracking;
weight the velocity field for each sector based on distances of the receive lines from the transmit beam axis to form weighted velocity fields;
interpolate the weighted velocity field of the first sector within the overlapping portion and the weighted velocity field of the second sector within the overlapping portion to adjust the weighted velocity fields of the first sector and the second sector; and
generate an image of a combined velocity field on the display by combining the weighted velocity fields, including the weighted velocity fields that are adjusted.

12. The medical imaging system of claim 11, wherein the controller circuit is configured to identify non-collinear ultrasound data from the ultrasound data, and generate at least one sub-image from the non-collinear ultrasound data.

13. The medical imaging system of claim 11, wherein the controller circuit is configured to weight the velocity field for each sector by applying a weighting signal that is linear and is centered about the transmit beam axis of the plurality of Tx beams transmitted into the sector.

14. The medical imaging system of claim 11, wherein the controller circuit is configured to interpolate by calculating a weighted mean of the weighted velocity fields within the overlapping portion.

15. The medical imaging system of claim 11, wherein the controller circuit is configured to shift the ultrasound data radially based on a registration model independently for each of the plurality of Tx beams.

16. The medical imaging system of claim 11, wherein the velocity field for each sector comprises a speckle pattern of velocities indicating the movement of the blood particles within the ROI.

17. The medical imaging system of claim 11, wherein the controller circuit is configured to determine a position of a second transmit beam axis of a second Tx beam from the plurality of Tx beams relative to a first transmit beam axis of a first Tx beam from the plurality of Tx beams such that portions of the first and second Tx beams overlap at the overlapping portion.

18. The medical imaging system of claim 11, wherein the controller circuit is configured apply clutter filtering to sub-images generated from the ultrasound data.

19. A computer implemented method, comprising:
transmitting a plurality of transmit (Tx) beams from an ultrasound probe into each sector of multiple sectors of a scan region that includes a region of interest (ROI), wherein the plurality of Tx beams into each sector are transmitted successively with respect to each other, the plurality of Tx beams are configured to acquire ultrasound data along receive lines by repeatedly firing the plurality of Tx beams along a transmit beam axis, at least a first sector of the sectors and a second sector of the sectors overlap each other at an overlapping portion;
performing speckle tracking for each sector by analyzing the ultrasound data acquired along the receive lines to calculate velocity data that represents movement of blood particles within the ROI, wherein the velocity data is calculated based on displacement of the blood particles identified in the ultrasound data acquired in response to successive Tx beams into the respective sector;
estimating a velocity field for each sector of the multiple sectors based on the velocity data calculated via the speckle tracking, the velocity field for each sector comprising a speckle pattern of velocities indicating the movement of the blood particles within the ROI;
weighting the velocity field for each sector based on distances of the receive lines from the transmit beam axis to form weighted velocity fields;
interpolating the weighted velocity field of the first sector and the weighted velocity field of the second sector by calculating a weighted mean of the two weighted velocity fields within the overlapping portion to adjust the weighted velocity fields of the first sector and the second sector; and
generating an image of a combined velocity field on a display by combining the weighted velocity fields, including the weighted velocity fields that are adjusted.

20. The computer implemented method of claim 19, further comprising adjusting a position of a second transmit beam axis of a second Tx beam from the plurality of Tx beams relative to a first transmit beam axis of a first Tx beam from the plurality of Tx beams such that portions of the first and second Tx beams overlap at the overlapping portion.

* * * * *